(12) United States Patent
Okamoto et al.

(10) Patent No.: US 6,548,020 B2
(45) Date of Patent: *Apr. 15, 2003

(54) REACTION SITE ARRAY WITH A BLACK MATRIX TO DECREASE CROSS-CONTAMINATION BETWEEN REACTION REGIONS

(75) Inventors: Tadashi Okamoto, Yokohama (JP); Nobuko Yamamoto, Isehara (JP); Tomohiro Suzuki, Atsugi (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/126,856

(22) Filed: Jul. 31, 1998

(65) Prior Publication Data

US 2002/0150506 A1 Oct. 17, 2002

(30) Foreign Application Priority Data

Aug. 1, 1997 (JP) .............................................. 9-207838

(51) Int. Cl.⁷ .......................... G01N 15/00; G01N 1/00; G01N 33/53; B01J 8/00; C12Q 1/68
(52) U.S. Cl. ........................ 422/68.1; 422/50; 422/129; 435/6; 435/7.1
(58) Field of Search .................. 422/50, 68.1, 129; 435/6, 7.1, 7.2; 530/333; 536/25.3

(56) References Cited

U.S. PATENT DOCUMENTS

| | | | |
|---|---|---|---|
| 4,000,334 A | * 12/1976 | Hallman et al. | ............... 427/56 |
| 5,143,854 A | 9/1992 | Pirrung et al. | ............... 436/518 |
| 5,202,231 A | 4/1993 | Drmanac et al. | ............... 435/6 |
| 5,424,186 A | 6/1995 | Fodor et al. | ................... 435/6 |
| 5,441,894 A | * 8/1995 | Coleman et al. | ............. 436/518 |
| 5,474,796 A | 12/1995 | Brennan | ..................... 427/213 |
| 5,688,642 A | 11/1997 | Chrisey et al. | ................ 435/6 |
| 6,110,426 A | * 8/2000 | Shalon et al. | ............... 422/68.1 |

FOREIGN PATENT DOCUMENTS

| | | |
|---|---|---|
| WO | WO89-10977 | 11/1989 |
| WO | WO93-22678 | 11/1993 |
| WO | WO95-25116 | 9/1995 |
| WO | WO95-35505 | 12/1995 |

OTHER PUBLICATIONS

Nucleic Acids Research, 1996, vol. 24 (15), pp. 3031–3039.
Chem. Pharm. Bull. vol. 29, No. 4 (1981) pp. 130–1135.
Khrapko, et al.; "Sequencing by Hybridization", J. DNA Seq. & Map. 1; 375–388, 1991.
Patent Abstracts of Japan, vol. 097, No. 006, 6/97 for JP R–054093.
Patent Anstracts of Japan, vol. 07, No. 010, 11/95 for JP-7–179797.
Chrisey, et al.; "Fabrication of patterned DNA surfaces", Nucleic Acids Research, vol. 24, No. 15, 1996, pp. 3040–3047.
Lemmo, et al.; "Characterization of an Inkjet . . . Synthesis", Anal. Chem., vol. 69, No. 4, Feb. 1997, pp. 543–551.

* cited by examiner

Primary Examiner—Ardin H. Marschel
(74) Attorney, Agent, or Firm—Fitzpatrick, Cella, Harper & Scinto

(57) ABSTRACT

A reaction site array to be used in conducting a plurality of reactions between two or more kinds of substances in a liquid medium with a trace amount is provided. The reaction site array comprises a plurality of reaction sites separated each other, each of the reaction sites is composed of a first region and a second region, the second region is raised from the first region to separate the first regions each other, and the first region has an affinity to the liquid medium and the second region has an affinity to the liquid medium lower than that of the first region. A preparation process of the reaction site array and a reaction process using the reaction site array are also provided.

6 Claims, 3 Drawing Sheets

REACTION SITE ARRAY WITH A BLACK MATRIX TO DECREASE CROSS-CONTAMINATION BETWEEN REACTION REGIONS

BACKGROUND OF THE INVENTION

1. Field of the Invention

The present invention relates to a reaction site array having plural reaction sites, the preparation process thereof, the reaction process using the reaction site array and a quantitative determination method of a substance in a sample solution using the reaction site array, for the use of screening of chemicals such as curative medicines, of gene fingerprinting, of gene sequencing by hybridization (SBH: Sequencing By Hybridization) and of simultaneous multi-detection of subject materials, which can be used for so-called combinatorial chemistry where plural reactions are carried out in a trace amount at the same time.

2. Related Background Art

Recently, so-called combinatorial chemistry has been attracting attention, in which, for example, a plurality of oligopeptides expected to interact with the target medicine are prepared, and the interaction between the oligopeptides and the various chemicals to be screened are analyzed, to identify the target medicine. Because the approach of random drug design is inefficient, and the evaluation of the designed and synthesized drugs with animal tests etc. is time consuming and expensive, combinatorial chemistry is now required as an alternative measure.

As probes for such a combinatorial chemistry, there are above-mentioned oligopeptides. As a means to bind such probes onto the solid, latex particles having functional groups on their surfaces to bind the probe are commercially available (Calbiochem—Novobiochem Inc.). Further, U.S. Pat. No. 5,143,854 discloses a preparation method of an oligopeptide array using photolytic protecting groups and a photolithography process in combination.

In detecting target nucleic acids having a certain base sequence by using a nucleic acid probe, instead of conventional methods such as Southern hybridization, a method has been proposed where plural types of nucleic acid probes are immobilized onto a solid support and then test samples including target nucleic acids are hybridized thereto and the detection is conducted as in combinatorial chemistry.

For example, Japanese National Publication of PCT Application No. 3-505157 discloses an analytical device for polynucleotide sequence which comprises the entire or specific parts of a full set of oligonucleotides with a certain length immobilized onto a support. Further, in U.S. Pat. No. 5,202,231, a similar analytical method for sequencing by hybridization of polynucleotide is proposed. In U.S. Pat. No. 5,424,186, a preparation process of a nucleic acid probe array onto a solid support by a combination use of photolytic protecting groups and a photolithography process is disclosed.

In enzyme-immunoassay, generally, reaction is carried out on a microplate having a maximum of 96 wells and the results are read by a microplate reader for simultaneous multi-item or multi-sample reaction and detection. This method has a limitation in high throughput analysis of a large number of samples.

One of the main concerns of combinatorial chemistry is how to supply various reaction species to a reaction site effectively; in other words, how to supply effectively a variety of reaction species each in a small amount (in a small liquid volume) to a reaction site without cross-contamination. From this viewpoint, the microplate method described above has theoretical limitations, although efficient and throughput systems have been developed recently using robot technology. It has another problem that a relatively large volume of liquid, i.e., from about 20 $\mu$l to about 100 $\mu$l, is necessary to be supplied to one well.

Also in the synthetic method of a probe array on a solid phase using a photolytic protection group and photolithography described in the above-mentioned U.S. Pat. Nos. 5,143,854 and 5,424,186, although it is possible to array a variety of probes onto a support, each probe lies on the same plane so that substances to be reacted with the probe are supplied to the entire probes, making it impossible to conduct different reactions with each probe. In addition, as the probes, oligopeptides or oligonucleotides which are synthesized on a solid support are used without any purifying treatment, and thus it is not possible to confirm whether desired probes are synthesized, and by-products which are inevitably synthesized during the probe synthesizing steps such as oligomers shorter than the probes etc. cannot be removed.

As a means to solve these problems, there has been proposed to supply reaction species already synthesized and purified to the reaction site using a microdispenser. For example, Khrapko et al. introduce a method to make a DNA probe array by spotting a DNA solution using a micropipet onto a polyacrylamide gel (J. DNA Sequencing & Mapping, 1, 375–388, 1991). According to this method, a DNA solution of a relatively small amount can is fed, but the region to which the DNA solution is fed cannot be specified, thus causing a problem in quantitation. Also, cross-contamination between the juxtaposed spots may occur when probe solutions are fed. The same problem may arise when the other reaction species are fed.

There has been also proposed a method for stepwise synthesis of nucleic acid probes performed on mainly porous solid matter, where the ink-jet method is employed to reduce the feeding amounts of reaction species and to achieve reactions in various kind and a large number (International Publication of PCT Applicatin No. WO95/25116). This method has problems in stepwise synthesis of probes and in the not-specified feeding regions.

There have been proposed some measures to solve the problem that the regions for the reaction species can not be specified.

Chrisey et al., for example, introduce a method where a silane coupling agent having appropriate functional groups is applied onto a support and subjected to patterning, then onto which DNA probe solutions are spotted to prepare a DNA probe array (Nucleic Acid Research, Vol.24, Number 15, 3040–3047, 1996).

Lemmo et al. introduce a method to feed reagents using a microdispenser into each well of a polypropyrene sheet (plate) molded to have a large number of wells on its surface (Anal. Chem., 69, 543–551, 1997). Specifically, a reagent solution of about 8 $\mu$l each is fed with a microdispenser into each well of a polypropyrene resin plate having 48×48 wells. The well size is presumed to be 3 mm in diameter and 2 mm in depth, and the size of the molded plate is described to be 8.5 inches×11 inches. With molding, the feasible well size is about several millimeters as in the above mentioned case, and when the whole plate size is considered, the number of wells composing the array is not more than 48×48, and the entire plate size is not so small. When actually used in combinatorial chemistry, many more kinds of probe species are desirably used and a much smaller plate is desirable. In addition, since a plate made of polypropylene is water repellent, it is difficult to distribute aqueous solutions of biomaterials such as nucleic acid into small wells, and undesirable cross contamination may occur between the adjacent wells.

Japanese National Publication of PCT Application No. 7-508831 discloses a method to supply a nucleic acid probe solution using a microdispenser to patterned regions of a silicone support. According to this method, both the probe species number and array size seem to fill the requirement, but there still remains the problem of cross contamination when probes are fed or when test samples are applied.

According to the method disclosed in International Publication of PCT Application No. WO95/35505, a nitrocellulose filter backed with a non water-permeable film is sectioned with silicone rubber and then to these sections a DNA solution is supplied to form a DNA array by non-covalent bonding. There is disclosed a method to examine plural samples at the same time without cross contamination by providing plural sets of sections divided with silicone rubber on the support, but not specifically about individual DNA reaction regions.

SUMMARY OF THE INVENTION

According to one aspect of the present invention, there provided is a process for producing a reaction site array which comprises a plurality of reaction sites to conduct a reaction between two or more kinds of substances in a liquid medium, each of the reaction sites being composed of a first region having a first affinity to the liquid medium and separated from each other by a second region having a second affinity to the liquid medium which is lower than the first affinity, and the second region being raised from the first region, the process comprising the steps of:

providing a support; and forming a matrix pattern having the second affinity and raised from the support surface, to form the first region composed of the support surface exposed corresponding to the matrix pattern and the second region composed of the matrix pattern.

According to another aspect of the present invention, there provided is a reaction site array comprising a plurality of reaction sites to conduct a reaction between two or more kinds of substances in a liquid medium, wherein each of the reaction sites is composed of a first region having a first affinity to the liquid medium and separated from each other by a second region having a second affinity to the liquid medium which is lower than the first affinity, and the second region is raised from the first region.

According to the further aspect of the present invention, there provided is a process for conducting a reaction between two or more kinds of substances in a liquid medium comprising the steps of:

providing a reaction site array comprising a plurality of reaction sites being composed of a first region having a first affinity to the liquid medium and separated from each other by a second region having a second affinity to the liquid medium which is lower than the first affinity, and the second region being raised from the first region, and applying the substances to at least one of the reaction sites and reacting the substances in the sites.

According to the further aspect of the present invention, there provided is a process for quantifying a first substance contained in a sample liquid comprising the steps of:

a) providing a reaction site array comprising a plurality of reaction sites, each of the reaction sites being composed of a first region having a first affinity to the sample liquid and separated from each other by a second region having a second affinity to the sample liquid which is lower than the first affinity, and the second region being raised from the first region;

b) supplying the sample liquid to the reaction site;

c) supplying to the reaction site a reagent providing a detectable and quantifiable signal when interacting with the first substance to enable the quantitative detection of the first substance; and d) quantitatively detecting the signal.

According to the present invention, the reaction sites are wells formed on a substrate in a matrix-like pattern, and the bottom (the first region) of the well is the exposed substrate having a high affinity to the liquid medium and the surrounding wall (the second region) raised from the substrate is made of a material having a low affinity to the liquid medium. Such a constitution enables smooth feeding of the reaction solution comprised of the liquid medium and reaction substances, prevention of the solution from flowing over the raised region because of the low affinity of the surface of the raised part to the solution, that is, prevention of cross contamination between the adjacent wells. Due to smooth feeding of the solution to the wells, the solution can be fed almost several ten times as much as the volume of the well.

According to the present invention, the reaction site array having such functions can be effectively prepared with high accuracy.

A matrix pattern forming wells can be made using a fine patterning technology described hereinafter, a large number of sufficiently small reaction sites can be made on a chip of, for example, 1 cm×1 cm.

In the present invention, that the support surface has an affinity to a liquid medium means, it has an affinity, in addition to the affinity to the liquid medium itself, to the liquid medium containing one or more substances such as reactants, auxiliaries required in reaction, reagents for quantitative or qualitative analysis, and reaction products. The same is said to the "non-affinity" of the projecting part has no affinity.

BRIEF DESCRIPTION OF THE DRAWINGS

FIG. 1A is a plan view and FIG. 1B is a cross-section.

DETAILED DESCRIPTION OF THE PREFERRED EMBODIMENT

Figure 1A:
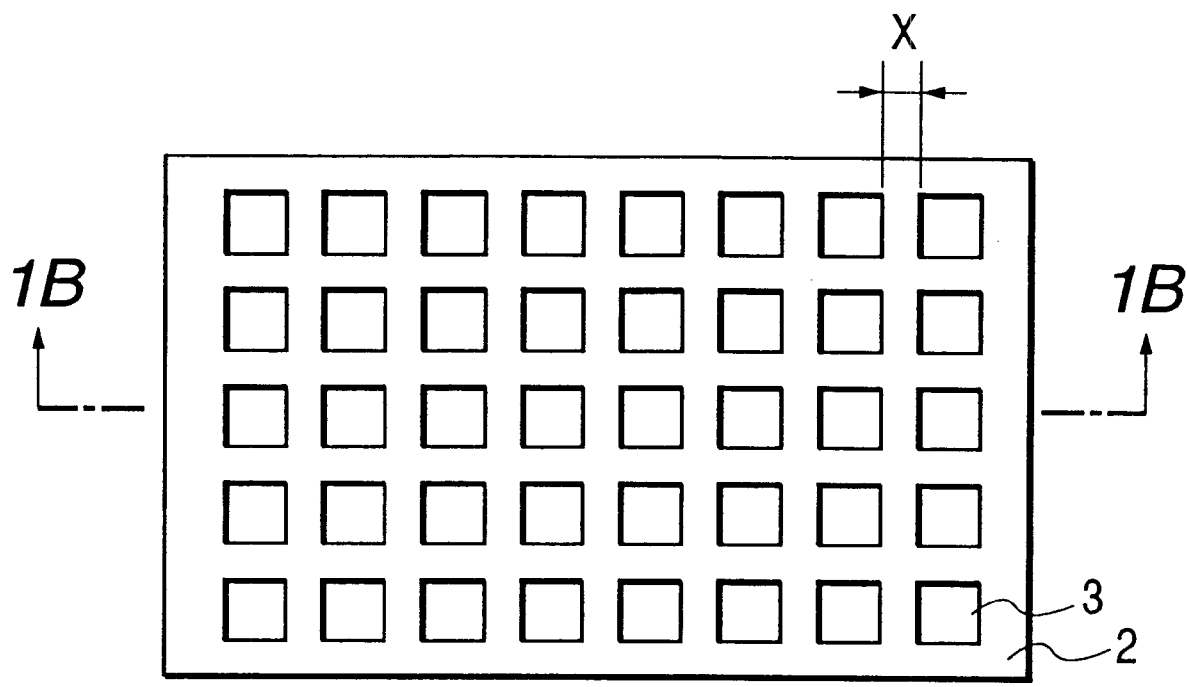
FIGS. 1A and 1B illustrate an example of the structure of the reaction site array of the present invention.
Figure 1B:
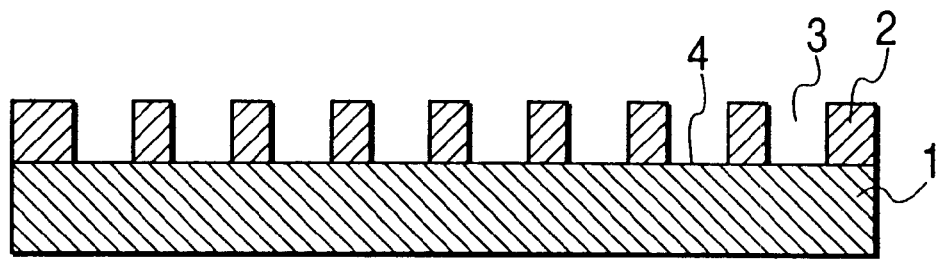

FIG. 1A is a plan view of a reaction site array according to one embodiment of the present invention and FIG. 1B is the cross-section through the line 1B—1B of FIG. 1A. This reaction site array has a plurality of wells 3 as reaction sites arrayed onto substrate 1 in a matrix form. The wells 3 are separated each other by projecting matrix pattern 2 raised from first region 4 of the well 3. The first region 4 is consisted of the exposed surface of the support 1, and the surface of the support 1 has an affinity to the liquid medium which is used for the reaction of, for example, two kinds of substances. On the other hand, the surface of the projecting matrix pattern 2 (the second region) has a low affinity to the liquid medium compared to the first region 4.

Specifically, when the liquid medium of the reaction system is an aqueous medium (water, or a liquid medium mainly containing water), it is preferable that the surface of the support 1 is hydrophilic and the surface of the projecting matrix pattern 2 hydrophobic. Contrary, when the liquid medium is not aqueous, it is preferable that the surface of the support 1 is lipophilic and the surface of the projecting matrix pattern 2 non-lipophilic.

More specifically, when the liquid medium is an aqueous one, the support 1 can be made of glass, metal or silicone wafer; glass, metal, silicone wafer, resin, or resin film those treated to have a hydrophilic surface; or glass, metal, silicone wafer, resin, or resin film those coated with a hydrophilic layer to have a hydrophilic surface, whereas the matrix pattern 2 can be made of a resin material to have a hydrophobic surface.

On the other hand, when the liquid medium is not aqueous, the support 1 can be made of a resin which can form a lipophilic surface, and the matrix pattern 2 can be made of metal, glass or the like to have a hydrophilic surface.

When the reaction is detected optically, preferably, the support to be used is transparent or in some cases optically black. As a preferable support, it can be used a support made of glass such as synthetic quartz, fused quartz and the like; of silicone wafer; of a resin such as acrylate, polycarbonate, polystyrene, and vinyl chloride, or a support in which a black pigment or dye has been mixed. As the black pigment, carbon black or organic black pigments can be used.

When the matrix pattern 2 is patterned by precision processing, the matrix pattern can be easily made from a photosensitive resin by light-exposing and developing the photosensitive resin.

In the present invention, it is preferable that the affinity to the liquid medium differs in the first region and the second region as much as possible. For example, when the liquid medium is an aqueous system, it is desirable that the substrate surface is more hydrophilic and the surface of the projected matrix pattern is more hydrophobic. In this case, it is possible to increase the hydrophobicity of the matrix pattern by baking the matrix pattern after light-exposure and development. Thus, this process is one of the preferable embodiments of the present invention. Likely, it also possible to increase the hydrophilicity of the first region by dry-etching the exposed support surface using the matrix pattern as a mask.

As a composing material of the matrix pattern used in the present invention, any material which meets the necessities of the present invention may be use. For example, metals such as chromium, aluminum and gold may also be used. When conducting an optical detection, the use of black chromium in combination with a clear support is believed to be ideal, from a view point of reliability, since it is highly opaque. But metal has relatively high hydrophilicity, and when a metal film is formed by evaporation considering the uniformity of the film thickness, the film formed is usually several thousand Angstrom thick. These features must be taken into consideration when a metal is utilized.

When the reaction system is an aqueous system, the first region should be hydrophilic. Thus, the suitable materials to form the matrix pattern are those having high hydrophobicity compared to the support and those which can form a film about 1 μm or more thick securedly, and resin materials such as acrylate, polycarbonate, polystyrene, polyethylene, polyimide, acrylic monomer, urethane acrylate, Teflon brand polytetrafluoroethylene and the like can be preferably used.

To make the matrix pattern, for example, the substrate is coated with a resin, and a photoresist is applied onto the resin on the substrate, and after patterning the photoresist, the resin is subjected to a patterning process such as etching. When a photosensitive resin is used, the resin itself can be patterned by a photolithographic process using a photo mask. As such photosensitive resins, UV resists, DEEP-UV resists, UV-curing resins and the like can be used. As the UV resists, negative type resists such as cyclized polyisoprene-aromatic bisazide resists, phenol resin-aromatic azide resists, and positive type resists such as novolac resin-diazonaphthoquinone resists are included.

Of DEEP-UV resists, as positive type resists, there are radiolytic polymeric resists such as polymethylmethacrylate, polymethylenesulphone, polyhexalfluorobutylmethacrylate, polymethylisopropenylketone, poly 1-trimethylsilyl propine bromide; and dissolution inhibitor resists such as O-nitrobenzyl cholate. As negative type DEEP-UV resists, there are polyvinylphenol-3,3'-diazidediphenylsulphone, glycidyl polymethacrylate and the like.

As ultraviolet-curing resins, included are polyester acrylate, epoxy acrylate and urethane acrylate containing 2 to 10% by weight of one or more photopolymerization initiators selected from benzophenon and substitution derivatives thereof, benzoin and substitution derivatives thereof, acetophenone and substitution derivatives thereof, and oxime compounds such as benzyl dioxime.

As mentioned above, the material used for making the matrix pattern preferably has opaque properties to increase the sensitivity and reliability of detection when an optical detection, for example, a fluorescent method is used. As such materials, there are metals, black resins or black photosensitive resins. As the black resins or black photosensitive resins, the above-mentioned resins, or photosensitive resins containing a black dye or a black pigment can be mentioned. As the black pigment, carbon black or black organic pigments can be used. Such a black-colored matrix pattern is called a black matrix pattern.

The shape of the first region can be selected considering the easy formation, handling performance, and operability at detection. Although the shape can be selected from various polygons, ellipticals and the like, a simple shape such as one illustrated in FIGS. 1A and 1B is desirable. The array pattern of the first regions can be changed appropriately according to necessity. For example, they may be arranged at the same intervals with the same separations as in the plan view shown in FIGS. 1A and 1B, or they may be arranged so that those in the adjacent lines may not stand side by side.

Considering the number of reactions and the total size of arrays, the longest width of the first region separated by the matrix pattern is preferably 300 μm or less. For example, if the plan shape of the well is a square as shown in FIG. 1A, the side length can be 200 μm or less. When the plan shape is to be rectangular, the length of the long side is preferably 200 μm or less, and when it to be a sphere, the diameter is preferably 200 μm or less. The lower limit of the size can be 1 μm.

The distance between the two adjacent first regions is preferably ranging from ½ fold to 2-fold of the longest width of the first region when the total size of the array, possibility of cross contamination, easy operation upon feeding of various solutions etc. are considered. The thickness of the matrix pattern (height from the support surface) is preferably 20 µm or less, considering the making of the matrix pattern, the volume of the well, and the volume of the reaction solutions to be supplied, especially when the matrix pattern is made by a photolithographic process. The lower limit of the thickness may be set to about 1 µm.

By setting the sizes in these ranges, a sufficient number of reaction sites can be provided. When the supply of the solutions into the first region for the reaction of two or more substances for combinatorial chemistry is carried out by the ink-jet recording method, the direction of ejected ink and the volume of ejected ink in the order of from picoliter to nanoliter as mentioned thereafter, are not always the same due to the changes in ejection conditions etc. Even in such a case, cross contamination among the adjacent first regions can be prevented by separating the first regions with projecting matrix pattern having the height of 1 µm or more.

When making the square wells of 200 µm×200 µm×20 µm, each inner volume becomes 800 pl, and when each distance x between the adjacent wells in the structure shown in FIGS. 1A and 1B is set to be 200 µm, the density of the minute reaction sites becomes 625 units/cm$^2$, i.e., reaction site densities of the order of 10$^2$ units/cm$^2$ or more fall into the scope of the present invention. Alternatively, when the wells are 5 µm×5 µm×4 µm in size and the distance between the adjacent wells is 5 µm, the volume of each well becomes 0.1 pl and the reaction site density becomes 1,000,000 units/cm$^2$. Because the patterning with the size of 5 µm×5 µm×4 µm is feasible by the today's microprocessing technology, the arrays in the order of 10$^6$ units/cm$^2$ or more also fall into the scope of the preset invention.

Next, the reaction using the reaction site described above will be illustrated.

In the present invention, in a certain well of the wells of the reaction site array of the structure described above, a reaction of at least two kinds of substances in a liquid medium can be carried out. In these wells, the same reaction or different reactions can be carried out simultaneously (including reactions of different reactants and different reactant concentrations).

To construct the reaction of the reactive system in the wells, any conventional methods can be utilized. For example, when two kinds of substances are reacted, a solution containing one substance is supplied into a well and then a solution containing the other substance is mixed therewith to initiate the reaction. When three substances are used, the methods where these substances are added to a certain well one by one to mix together, where a solution containing two substance and another solution containing the remaining one are supplied into a well to mix together.

When the wells are formed as minute reaction sites and the volumes of the reaction solutions are as small as from sub-picoliter to sub-nanoliter, it is preferable to take a means to prevent evaporation and/or gaseous diffusion of the fed solutions into the reaction site. For example, when the reaction system is an aqueous system, it is desirable to place the array under the conditions of necessary constant temperature and constant humidity.

In the present invention, the volume of the liquid supplied at the reaction is around from 0.1 pl to 1 nl according to the above-mentioned calculation, presuming the same amount as that of the well is fed. In the present invention, since the matrix pattern part has little affinity to the liquid to be supplied, with some liquid species, it is possible to feed the extra amount of the liquid exceeding the volume of the well, so that the liquid stays swelling by surface tension at the well opening. In this case, for example, the solution volume of from ten- to several ten-fold of the well volume can be supplied. In other words, in the above-mentioned case, the liquid of from several picoliter to tens of nanoliter can be supplied. In any case, it is often difficult to supply a liquid of such a small amount with good precision both in terms of location and amount using a regular microdispenser or micropipet. Thus, it is preferable to supply the reaction solutions into the well using the ink-jet method in the present invention.

A solution for the reaction system can be fed by the ink-jet method, using an ink-jet head used in an ink-jet printer. In the ink-jet printing, ink is ejected with highly precise positioning of an µm order, making it highly suitable to the supply of the reaction system into a minute reaction site array of the present invention. Since the amount of the ejected ink is from about 1 pl to about several nl in general, it is also suitable to feed the reaction system solution in the present invention. Because the ink-jet heads are manufactured using semiconductor manufacturing technology, the discharging amount can further be adjusted to the desired volume.

Although the stepwise synthesis of a DNA probe array using such an ink-jet method is mentioned in International Publication of PCT Application No. WO95/25116, the substrate disclosed in it is of simple glass or of porous glass. When a simple glass substrate is used, the region where the applied solution spreads can not be controlled and also the problem of cross contamination will occur. When a porous glass substrate is used, the solution spreading can be controlled to some extent, but not in a quantitative way, and the problem of cross contamination still remains. Moreover, with the inkjet method, a certain extent of fluctuation occurs in the direction of droplet ejected from the head, which results in the disorder of the array when a simple glass or the porous glass substrate is used. On the other hand, according to the present invention, the spreading of the droplet can be quantitatively regulated by the projecting matrix pattern, and even if the fluctuation in the discharging direction occurred and the ejected droplet does not hit the first region precisely, the non-affinity of the matrix pattern to the ejected droplet leads the droplet into the desired first region.

As the ink-jet method usable in the present invention to supply a reaction system solution to the reaction site, there is the piezo-jet method, or the bubble-jet method utilizing thermal bubbling.

Next, the reaction species highly suitable to the reaction using the reaction site array of the present invention will be described. In the present invention, any reaction species which can react in the wells arranged in an array may be used. But, the liquid medium of the reaction system must be an aqueous system, when the first region is hydrophilic and the surface of the projecting matrix pattern is hydrophobic, and the liquid medium should be an organic solvent, when the bottom of the well (first region) is lipophilic and the surface of the projecting matrix pattern is non-lipophilic. When two or more kinds of solutions are to be supplied, it is desirable that the solvents composing the solutions are compatible.

Reaction species used in the present invention are exemplified by, a ligand and a receptor thereof, an oligo- or polypeptide having a certain amino acid sequence and a substance having an affinity thereto, an enzyme and a substrate thereof, an antigen and an antibody to the antigen, a nucleic acid or nucleic acid analog having a certain base sequence and a nucleic acid or nucleic acid analog having a complementary base sequence to a certain base sequence of the former nucleic acid or nucleic acid analog. The nucleic acid or nucleic acid analog is exemplified by DNA, RNA, or PNA. PNA is a nucleic acid analog having a peptide bond backbone (protein nucleic acid).

Also, an embodiment where at least one of the reaction substances is bound to the inner surface of the well is in the scope of the present invention. Such reaction species are exemplified by immobilized enzymes, immobilized antibodies, immobilized nucleic acid probes, immobilized peptide probes and the like can be exemplified. By immobilizing at least one reactive substances, the supply of the other reactive species becomes easy and at the same time operations such as washing becomes easy.

Next, a preparation process of the reaction site array using a clear glass substrate and a black photosensitive resin for the matrix pattern is explained. Reaction in the array thus formed is also explained.

(1) A clear glass substrate is appropriately washed, dried, and then a black photosensitive resin is applied thereto. As the application method, various methods including spin coating, die coating, and dip coating can be used.

(2) The applied layer is subjected to interim hardening using, for example, a hot plate. And then, the layer is exposed to light using a photo mask having a certain pattern and an exposure device of a wave length matching to the spectral sensitivity of the photosensitive resin.

(3) Then development follows: when the photosensitive resin composition is a negative-type, the part shielded from light with the mask is washed out by the developing solution to expose the substrate surface and the light-exposed part remains as a black matrix pattern. Then the substrate is rinsed to remove the developing solution and dried.

(4) The matrix is hardened again using, for example, a hot plate to confer it the required water repellency.

(5) The substrate is subjected to dry etching using the black matrix as a mask to clean the engraved part in the matrix pattern to the required cleanness.

(6) A solution (an aqueous solution in this case) of the substance(s) to be reacted is injected into the well at the desired position of the matrix pattern by the bubble-jet method.

(7) The reaction site array is placed under predetermined reaction conditions.

(8) The necessary detection operations are carried out.

The present invention will be specifically illustrated with examples thereinafter.

EXAMPLE 1

Preparation of a Micro Reaction Site Array with a Black Matrix (for an Aqueous Reaction System)

A synthetic quartz substrate was washed by sonication with an aqueous 2% sodium hydroxide solution, and treated with UV-ozone. A DEEP-UV resist containing carbon black (BK-739P, product of Shin-Nittetsu Kagaku Inc., a negative-type resist for black matrix) was applied by spin coating to make the film thickness 5 $\mu$m after hardening. The coated substrate was placed on a hot plate to heat at 80° C. for 5 min to harden the resist.

The coated substrate was then subjected to proximity exposure using a DEEP-UV exposure devise and a pattern mask to constrain the width of the black matrix pattern (corresponding to the distance between the wells: x, as shown in FIGS. 1A and 1B, the same expression will be used hereinafter) to 200 $\mu$m and the size of the square wells to 200 $\mu$m×200 $\mu$m, Then the black matrix pattern was formed using an inorganic alkaline aqueous solution as a developing solution and a spin developer, and then rinsed with pure water to completely remove the developing solution. After drying using a spin dryer, the product was heated in a clean oven at 180° C. for 30 min to harden the black matrix completely.

Then, the substrate surface in each well was cleaned by plasma ashing using the black matrix as a mask. At this point, the measured contact angle of the black matrix surface to water was 87° indicating little wettability, and the contact angle of the substrate surface to water was 22° indicating considerable wettability.

EXAMPLE 2

Preparation of a Minute Reaction Site Array Using Black Chromium (for a Non-aqueous Reaction System)

An acrylic resin substrate (Deraglass, product of Asahi-Kasei Kogyo) was washed by sonication with a 2% sodium hydroxide aqueous solution and treated with UV-ozone. The resist pattern corresponding to the first regions was formed by conventional photolithography. The thickness of the resist was 1 $\mu$m after hardening. After the post-baking process at 100° C. for 30 min, a black chromium film of 2000 angstrom thick was made, and the chromium film corresponding to the first regions was removed by the lift-off method using a resist exfoliating solution. The support was washed appropriately and after drying, the support surface was cleaned by plasma ashing as described in Example 1. By this process, the minute reaction site array having a matrix pattern made of black chromium and first regions made of acrylic resin was obtained. At this point, the measured contact angle of the black chromium surface with water was 25°, indicating wettability, and the contact angle of the substrate surface with water was 93°, indicating little wettability.

EXAMPLE 3

Supply of an Aqueous Solution into a Minute Reaction Site Array by Ink-jet Method—I A minute reaction site array of 1 cm×1 cm was made on a glass substrate, which was comprised of 2500 units of square first regions of 100 $\mu$m×100 $\mu$m (reaction well) with the black matrix pattern of which width was 100 $\mu$m, by the same manner as described in Example 1. Then, an aqueous 10 $\mu$M rhodamine B was fed into the wells in a checkered pattern using an ink-jet device, where the feed amount per well was 50 pl, equal to the volume of the reaction well. The precision of ejection positioning of the ink-jet devise used was ±2.5 $\mu$m. Then, an aqueous solution of 10 $\mu$M amino-FITC was supplied in an amount of 50 pl per well to the remaining reaction wells from another ink-jet head. Rhodamine B and amino-FITC were used because they are water soluble and their fluorescence is suitable for observation of conditions of the distributed liquid and cross contamination.

Using a Nikon fluorescent microscope with a G excitation filter (for rhodamine B) and a B excitation filter (for amino-FITC), the conditions of fed solutions were observed by fluorescence at the magnification of 100 times. Each solution was uniformly distributed into the wells without forming a droplet. Moreover, the fluorescence of each dye was found only in the wells where the dye should be found, indicating that the distribution of the solution into wells was carried out without any cross contamination.

EXAMPLE 4

Supply of an Aqueous Solution into a Minute Reaction Site Array by Ink-jet Method—II Solutions of rhodamine B and amino-FITC were distributed in the same manner as in Example 3, except that 500 pl, 10 times as much as the well volume, was distributed to each well. When observed using a fluorescent microscope, each dye solution was supplied into each well forming a droplet due to the water repellency of the matrix pattern. No cross contamination was observed as in Example 3.

EXAMPLE 5

Supply of a Non-aqueous Solution into a Minute Reaction Site Array by Ink-jet Method A minute reaction site array of 1 cm×1 cm was formed on an acrylic substrate, which was comprised of 2500 units of square first regions of 100 $\mu$m×100 $\mu$m (reaction well) with the black chromium matrix pattern of which width was 100 $\mu$m, in the same manner as in Example 2. Then, a DMSO solution of 10 $\mu$M rhodamine B was supplied in the 50-fold volume of the well volume, 50 pl per well, to every other well in a checkered pattern using an ink-jet device. Then, the same amount of a DMSO solution of 10 $\mu$M FITC was supplied into each remaining well from another ink-jet head. When observed using a fluorescent microscope, the DMSO solution of each dye was supplied into each well swollen from the well (because the supplied volume was not large enough to form a droplet) due to the non-lipophilic property of the matrix pattern. Also no cross contamination was observed as in Example 3.

EXAMPLE 6

Feeding Model of Two Kinds of Aqueous Solutions into a Minute Reaction Site Array by Ink-jet Method In the same manner as in Example 3, the aqueous rhodamine B solution and the amino-FITC solution were distributed in a checkered pattern to the wells as a model of the first reaction species, except that each well received 250 pl of the solution, 5 times as much as the well volume. Then, another 250 pl of the same solution was added to the same well as a model of the second reaction species. When observed using a fluorescent microscope, each solution had been distributed in each well in the form of a droplet due to the water repellent property of the matrix pattern, and no splash was observed in swelle of the second feeding. Also no cross contamination was observed.

EXAMPLE 7

Supply of Two Kinds of Aqueous Solutions into a Minute Reaction Site Array by Ink-jet Method and Their Reaction Fifty picoliter of a TE buffer (pH 7.5) containing 40 $\mu$M sonication-fragmented salmon testes DNA was distributed into each well as in Example 3. Then, 50 pl of a TE buffer containing 10 $\mu$M ethidium bromide (EB) was added to the same well, and then incubated for 5 min in an incubator at 25° C. and 100% humidity, and the fluorescence was observed using a fluorescent microscope (with a G excitation filter). The fluorescence was observed in the wells received both solutions. This means that EB and the double-stranded nucleic acid reacted in the well and the fluorescence due to the EB intercalation was observed. From the wells to which only EB was supplied (control wells), only very weak fluorescence was observed.

EXAMPLE 8

Figure 2:
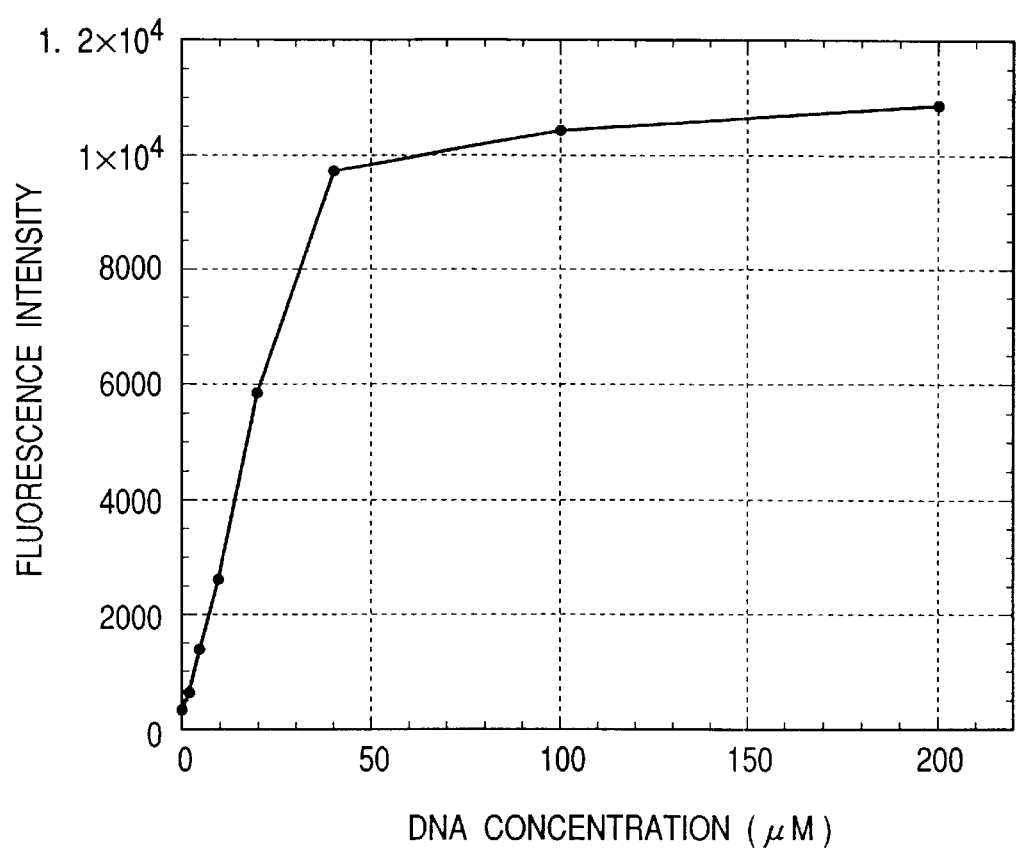
FIG. 2 is a graph which illustrates the results of quantitative determination of fluorescent intensity of Example 8.

Supply of Two Kinds of Aqueous Solutions into a Minute Reaction Site Array by Ink-jet Method, Their Reaction and Quantitation of Fluorescence After the Reaction—I DNA solutions of 0 $\mu$M, 2 $\mu$M, 5 $\mu$M, 10 $\mu$M, 20 $\mu$M, 40 $\mu$M, 100 $\mu$M and 200 $\mu$M (base pair concentration) were supplied in an amount of 50 picoliter into eight wells respectively, as in Example 7. Then, 50 pl of a 10 $\mu$M EB solution was added to each well, and incubated as in Example 7. Then the fluorescent images from the fluorescent microscope were read into an ICCD camera (Hamamatsu Photonix C2400-87) and the light volume was quantitatively determined by an image processing devise (Hamamatsu Photonix Argus50). The signal amplification level of Argus50 was appropriately set. The results are shown in FIG. 2. FIG. 2 indicates that the reaction in the minute reaction site array of the present invention proceeded and detected quantitatively. At a certain ratio of DNA and EB, the fluorescence intensity reaches the saturation.

EXAMPLE 9

Figure 3:
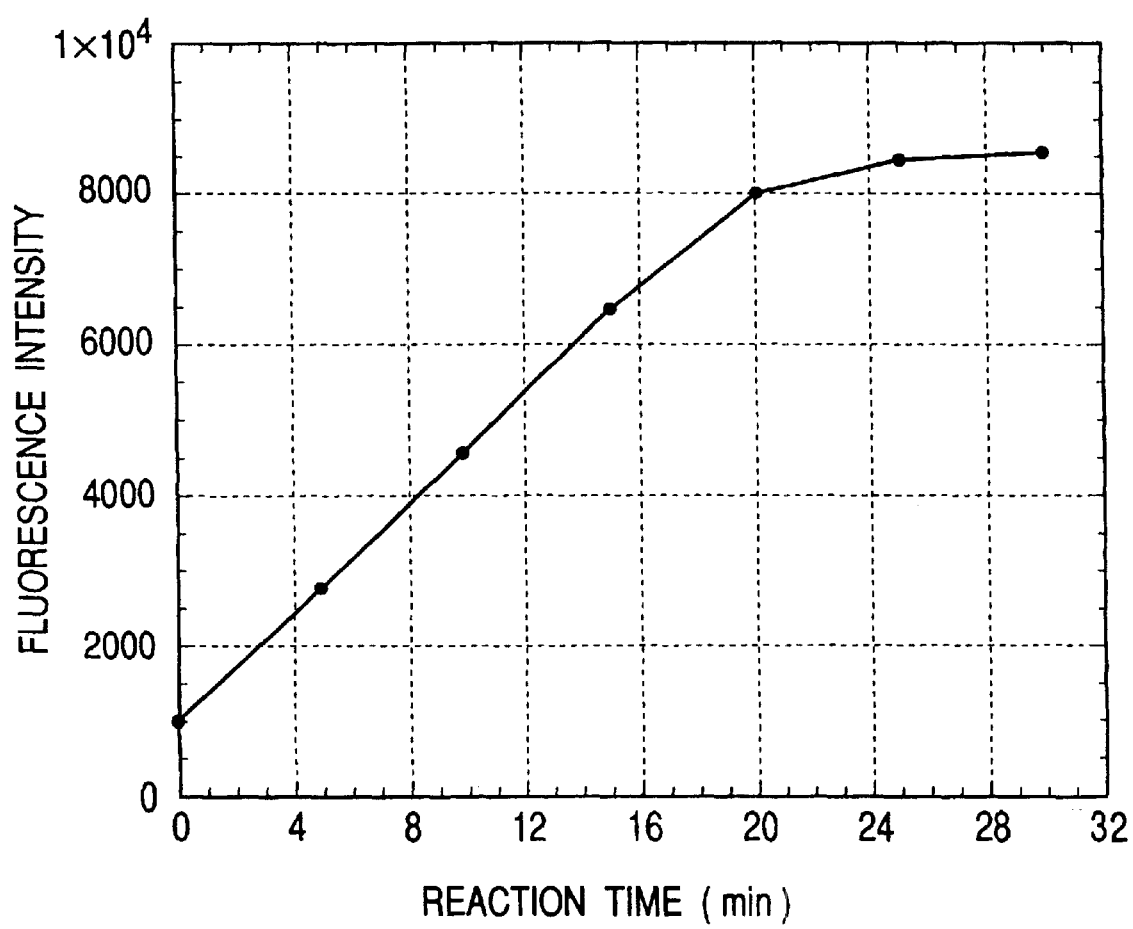
FIG. 3 is a graph which illustrates the results of quantitative determination of fluorescent intensity of Example 9.

Supply of Two Kinds of Aqueous Solutions into a Minute Reaction Site Array by Ink-jet Method, Their Reaction and Quantitative Determination of Fluorescence After the Reaction—II A 40 $\mu$M TE buffered (pH 7.5) solution of carboxyfluorecein diacetate (Molecular Probe Inc., C-369), a fluorescent substrate of esterase, was fed by ink-jet method in an amount of 50 pl each into seven wells of the minute reaction site array prepared in the same manner as described in Example 3. Then, a solution of 2 units/liter choline esterase (Wako Jyunyaku) in TE buffer (pH 7.5) was added to each well with different time intervals so that the reaction time in the seven wells becomes 0 min, 5 min, 10 min, 15 min, 20 min, 25 min and 30 min, respectively. The reaction was conducted in an incubator at 25° C. and 100% humidity. Then, after the heat treatment at 60° C. for 5 min to inactivate the enzyme, the fluorescence of carboxyfluoresceine which was produced by the enzyme digestion was observed and quantitated by a fluorescent microscope (with a B excitation filter)+ICCD+Argus. The signal amplification level of Argus50 was the same as described in Example 8. The results are shown in FIG. 3. FIG. 3 indicates that the reaction in the minute reaction site array of the present invention proceeded and detected quantitatively. The fluorescence intensity reaches the saturation due to the enzyme/substrate ratio.

EXAMPLE 10

Preparation of a More Minute Reaction Site Array and Supply of an Aqueous Solution by Ink-jet Method A minute reaction site array of about 1 cm×1 cm was formed on a glass substrate in the same manner as in Example 1, except that the black matrix pattern was 5 $\mu$m in width and the film thickness was 4 μm, and there contained 1,000,000 units of 5 μm×5 μm square wells. Then, a solution of 10 μM rhodamine B was fed to each well using an ink-jet device in a checkered pattern. The precision of ejection positioning of the ink-jet devise used is ±0.5 μm. Then, an aqueous solution of 10 μM amino-FITC was fed in an amount of 1 pl into each of the remaining wells from another ink-jet head.

By using a Nikon fluorescent microscope installed with a G excitation filter (for rhodamine B) and a B excitation filter (for amino-FITC), and fluorescence observation was carried out at the magnification of 400 times to know the conditions of the fed solutions. The solution of each dye was found in the form of droplet as in Example 4. No cross contamination was observed.

The present invention enables the preparation of a minute reaction site array suitable for the supply of the reaction species to conduct a large number of various kinds of reactions in a small region (for example, 1 cm×1 cm) on a substrate. With combined use of the ink-jet method, supply of solutions of reaction species to the minute reaction site array of the present invention and their reaction, as well as detection of the reaction and quantitative determination as needed have been able to conducted.

What is claimed is:

1. A reaction site array for receiving a liquid medium containing a reactant comprising a substrate and a black matrix arranged on a surface of the substrate, wherein (i) a difference in wettability to a liquid medium between the black matrix and a region of the substrate not provided with the black matrix is sufficiently large to decrease cross-contamination; (ii) said region is a reaction site; (iii) the liquid containing the reactant introduced on a surface of said region reacts on the surface of said region; (iv) the black matrix is composed of a resin, which is obtained by using a photosensitive resin, and one of a black pigment or carbon black; and (v) the region is more wettable by the liquid medium than the black matrix.

2. A reaction site array for receiving a liquid medium containing a reactant comprising a substrate and a black matrix arranged on a surface of the substrate, wherein (i) a difference in wettability to a liquid medium between the black matrix and a region of the substrate not provided with the black matrix is sufficiently large to decrease cross-contamination; (ii) said region is a reaction site; (iii) the liquid containing the reactant introduced on a surface of said region reacts on the surface of said region; (iv) the black matrix is composed of a metal; and (v) the region is more wettable by the liquid medium than the black matrix.

3. The reaction site array according to claim 2, wherein the metal is chromium, aluminum or gold.

4. A reaction site array for receiving a liquid medium containing a reactant comprising a substrate and a black matrix arranged on a surface of the substrate, wherein (i) a difference in wettability to a liquid containing a reactant between the black matrix and a region of the substrate not provided with the black matrix is sufficiently large to decrease cross-contamination; (ii) said region is a reaction site; (iii) said region is adapted to receive a DNA probe or an RNA probe; (iv) the liquid containing the reactant introduced on a surface of said region reacts on the surface of said region; (v) the black matrix is composed of a resin, which is obtained by using a photosensitive resin, and one of a black pigment or carbon black; and (vi) the region is more wettable by the liquid medium than the black matrix.

5. A reaction site array for receiving a liquid medium containing a reactant comprising a substrate and a black matrix arranged on a surface of the substrate, wherein (i) a difference in wettability to a liquid containing a reactant between the black matrix and a region of the substrate not provided with the black matrix is sufficiently large to decrease cross-contamination; (ii) said region is a reaction site; (iii) said region is adapted to receive a DNA probe or an RNA probe; (iv) the liquid containing the reactant introduced on a surface of said region reacts on the surface of said region; (v) the black matrix is composed of a metal; and (vi) the region is more wettable by the liquid medium than the black matrix.

6. The reaction site array according to claim 5, wherein the metal is chromium, aluminum or gold.

* * * * *

UNITED STATES PATENT AND TRADEMARK OFFICE
CERTIFICATE OF CORRECTION

PATENT NO. : 6,548,020 B2
DATED : April 15, 2003
INVENTOR(S) : Tadashi Okamoto et al.

It is certified that error appears in the above-identified patent and that said Letters Patent is hereby corrected as shown below:

<u>Title page</u>,
Item [57], ABSTRACT,
Line 4, "separated" should read -- separated from --; and
Line 7, "each" should read -- from each --.

<u>Column 2</u>,
Line 31, "is" should read -- be --.

<u>Column 4</u>,
Line 42, "to" should read -- of -- and "has" should read -- regarding having --.

<u>Column 10</u>,
Line 2, "$\mu$m ," should read -- $\mu$m. --.

<u>Column 11</u>,
Line 54, "swelle" should read -- wells --.

Signed and Sealed this

Eleventh Day of November, 2003

JAMES E. ROGAN
*Director of the United States Patent and Trademark Office*